US00PP35772P2

(12) United States Plant Patent
Korlipara

(10) Patent No.: US PP35,772 P2
(45) Date of Patent: Apr. 23, 2024

(54) ***RUDBECKIA* PLANT NAMED 'SUN STREAM'**

(50) Latin Name: *Rudbeckia fulgida*
Varietal Denomination: Sun Stream

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/215,270

(22) Filed: Jun. 28, 2023

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./263.1, 474
See application file for complete search history.

*Primary Examiner* — Karen M Redden
(74) *Attorney, Agent, or Firm* — The Webb Law Firm

(57) ABSTRACT

A new and distinct *Rudbeckia* plant having flat, yellow-orange colored ray florets, a medium, upright habit, and excellent vigor.

2 Drawing Sheets

Botanical classification: *Rudbeckia fulgida.*
Varietal denomination: 'Sun Stream'.

BACKGROUND OF THE NEW PLANT

The present invention is a new and distinct *Rudbeckia* plant having the varietal name 'Sun Stream'. *Rudbeckia* is in the family Asteraceae. 'Sun Stream' is a selection from a planned breeding program that originated from a controlled cross between unnamed, unpatented, and proprietary seedlings. The seed parent was a *Rudbeckia hirta* hybrid having a small habit with very double, yellow to orange petals. The pollen parent was a *Rudbeckia fulgida* variety. Both parental varieties are now extinct. As such, any further comparisons to the claimed variety cannot accurately be provided.

Compared to *Rudbeckia* plant named 'Goldsturm' (unpatented), the new cultivar has double and not single flowers. Compared to *Rudbeckia* plant named 'Henry Eilers' (unpatented), 'Sun Stream' has double flowers and is much shorter with better branching than 'Henry Eilers'.

The new variety has only been reproduced by asexual propagation (cuttings and tissue culture). Each of the progeny exhibits identical characteristics to the original plant. Asexual propagation by cuttings and tissue culture using standard micropropagation techniques with terminal and lateral shoots performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Rudbeckia* plants known to the breeder, the new variety is characterized by the following:

1. Inflorescences with flat, yellow-orange colored ray florets;
2. A medium, upright habit; and
3. Excellent vigor.

DESCRIPTION OF THE DRAWINGS

The accompanying photographic drawings illustrate the new variety at approximately 6 months of age, with the colors being as nearly true as possible with color illustrations of this type.

DETAILED BOTANICAL DESCRIPTION

Figure 1:
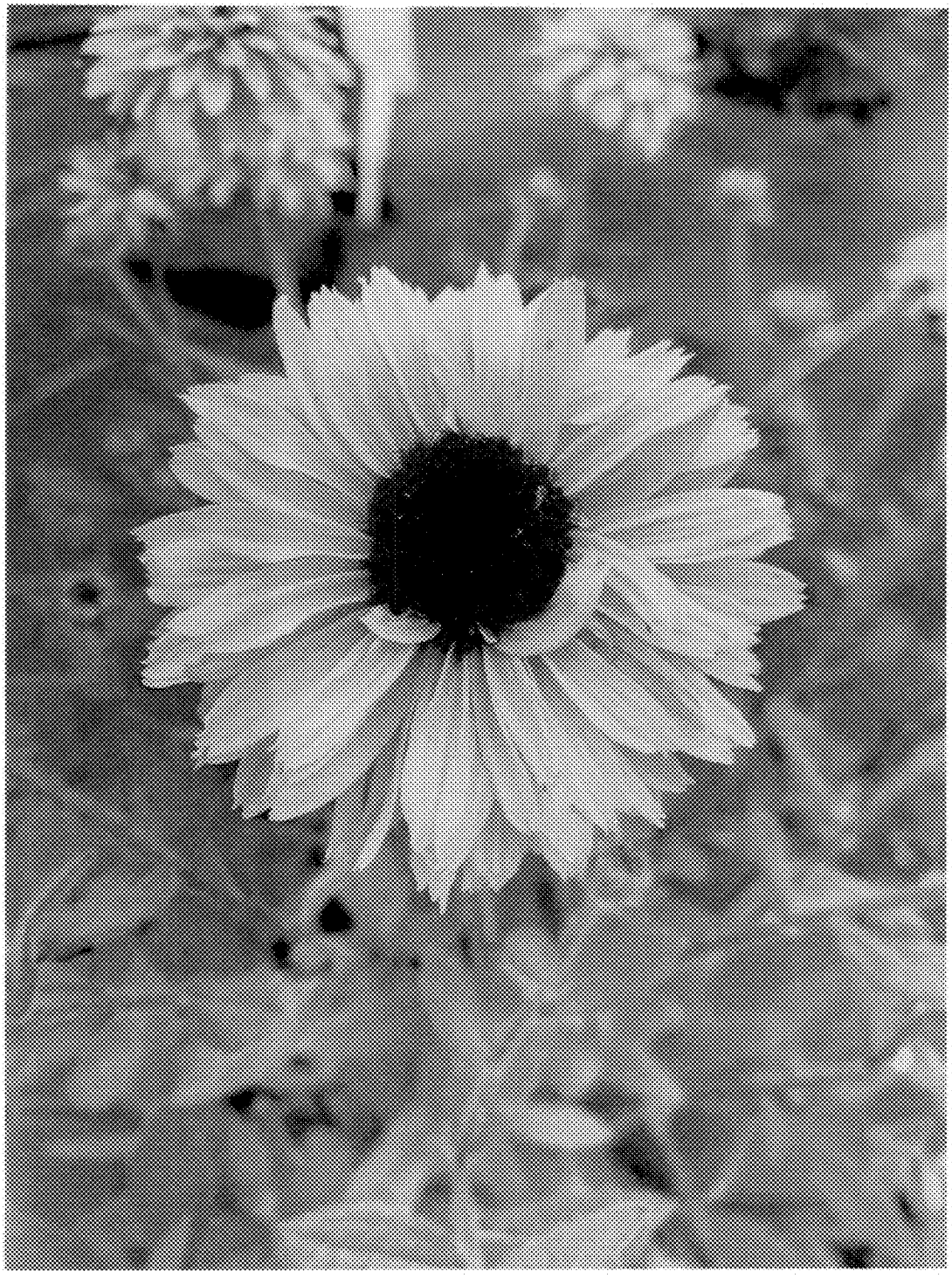
FIG. 1 illustrates a close-up view of the new variety in Canby, Oregon.
Figure 2:
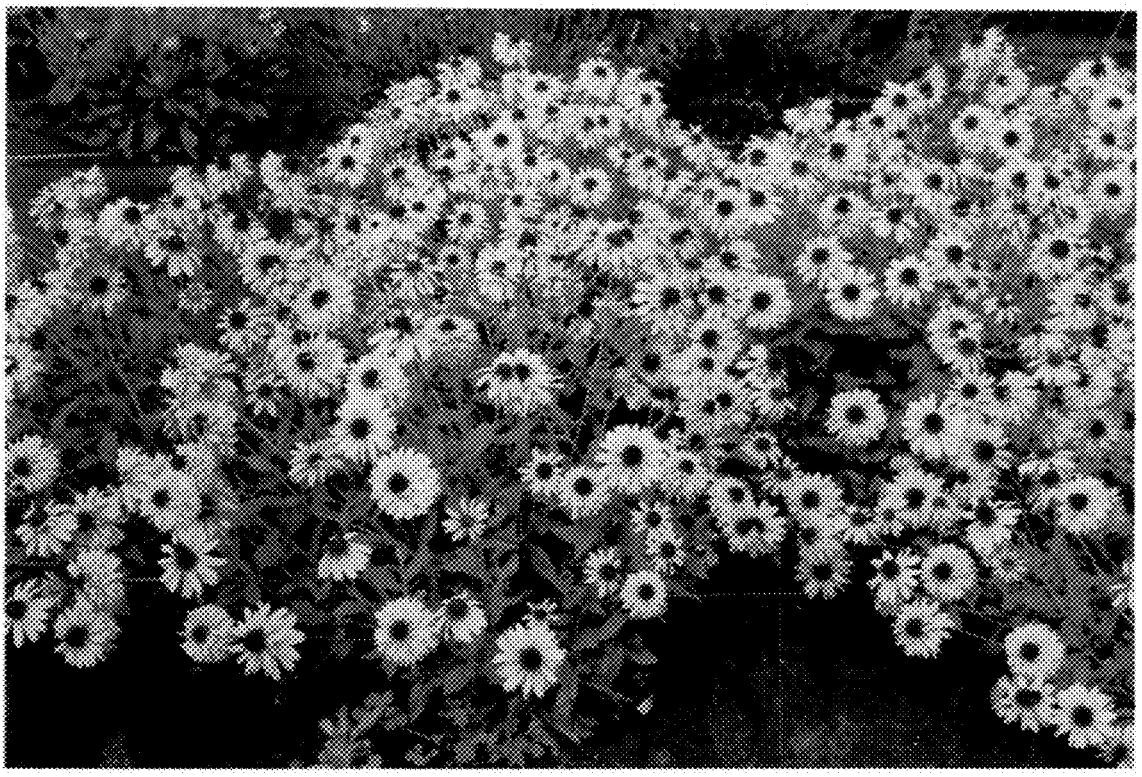
FIG. 2 illustrates plants of the new variety in the field in full sun in Canby, Oregon in early August.

The following is a detailed description of the new variety based on observations of 6-month-old plants that were grown outside under full sun in Canby, Oregon (USDA Zone 8). Temperatures range from a high of 35° C. in August to a low of 0° C. in January. Normal rainfall in Canby, Oregon is around 1 m per year. Color references are based on The 2007 R.H.S. Colour Chart of The Royal Horticultural Society of London, 5$^{th}$ Edition.

Plant:

*Type.*—Herbaceous annual.
*Hardiness.*—USDA Zones annual.
*Size.*—50.0 cm wide and 50.0 cm tall from the top of the soil to the top of the inflorescences.
*Form.*—Basal clump, with about 30 stems from the base.
*Vigor.*—High.

Flowering stems:

*Type.*—Ascending, branching where flowering only.
*Inflorescences per stem.*—From 3 to 7.
*Size.*—About 10.0 cm tall to the start of a flowering branch and 3.0 to 3.5 cm wide at the base.
*Internode length.*—From 4.0 cm to 5.0 cm.
*Texture.*—Strigose.
*Color.*—RHS 187B at the upper portion and RHS 187A near the base.

Leaf:

*Type.*—Simple.

*Arrangement*.—Alternate, occasionally whorled in threes.

*Shape*.—Lanceolate.

*Size*.—Overall to 8.0 cm long and 2.0 cm wide, terminal leaflets grow to 7.5 cm long and 2.5 mm wide, and lateral leaflets grow to 5.0 cm long and 2.0 cm wide.

*Margin*.—Serrate.

*Apex*.—Acute.

*Base*.—Attenuate.

*Texture*.—Strigose on both sides.

*Venation*.—Pinnate, with 3 main veins extending from the base on each leaflet.

*Upper surface color*.—RHS 137C, with venation color of RHS 137C.

*Lower surface color*.—RHS 147B, with venation color of RHS 137C.

*Petiole*.—Length: To 1.0 cm. Width: 4.0 mm, measured above the clasp. Texture: Strigose. Color: RHS 145C.

Inflorescence:

*Type*.—Composite.

*Number of flowering branches from stem*.—3 to 7.

*Flowering stem*.—Grows to 34.0 cm tall from the start of the flowering branches to the base of the terminal inflorescence and 5 to 10 side branches grow to 10.0 cm to 17.0 cm taller than the terminal inflorescence. The cluster of inflorescences grows to 12.0 cm long and 10.0 cm wide. The peduncle grows to 21.0 cm long, is RHS 146C in color, with sparse, strigose hairs that are 1.0 mm in length and RHS 187A in color. The leaves on the flowering branches are simple, linear to cuneate in shape, and grow to 7.5 cm long and 2.0 cm wide. Their margins are serrate, base attenuate, tip acute, and have an upper surface color of RHS 137B, lower surface color of RHS 137D, and venation color of RHS N137B.

*Width*.—To 7.0 cm.

*Depth*.—1.5 cm.

*Form*.—Ray florets are held mostly horizontally and a mature disc is rounded and flattened.

*Bloom period*.—May through October in Canby, Oregon.

*Lastingness on the plant*.—About 2-3 weeks in Canby, Oregon.

*Fragrance*.—None.

*Fertility*.—Low.

Flower bud (immature inflorescence):

*Form*.—Ray florets held upright and tubular.

*Width*.—1.8 cm.

*Depth*.—0.75 cm.

*Color*.—Ray florets: RHS 144A and tinted RHS N144B. Disc: RHS 200A.

Ray florets:

*Number*.—From 25 to 30.

*Shape*.—Linear, with the apex being 4-lobed — each lobe is ovate in shape, with entire margins and acute tips.

*Length*.—3.0 cm.

*Width*.—10.0 mm.

*Margin*.—Entire.

*Texture*.—Upper surface: Pubescent. Inner surface: Glabrous.

*Color* (*both surfaces*).—RHS 172B at the base, with the apex being RHS 21A. The bottom surface has a tint of RHS 17A present.

*Pistil*.—None.

*Stamen*.—None.

Disc/disc florets:

*Disc*.—Shape: Rounded. Depth: To 9.0 mm. Width: To 20.0 mm. Color: RHS 200A.

*Disc florets*.—Number: About 170 and bisexual. Shape: 5-lobed (triangular lobes) with a tubular, glandular corolla. Overall length: 4.0 mm. Overall width: 1.5 mm. Corolla length: 3.0 mm. Corolla width: 1.5 mm. Color: RHS N186A. Pistil: 1; 6.0 mm long; RHS N186B. Ovary: 3.0 mm long; RHS NN155B. Style: 4.0 mm long; RHS N186A. Stigma: 2-branched; RHS 186C. Stamen: 5; 6.0 mm long; RHS 187A. Pollen: None present.

Phyllaries:

*Description*.—3 leafy series that grow in area to 4.0 cm wide and 3.0 mm deep.

*Lobes*.—Shape: Cuneate and slightly reflexed. Length: 20.0 mm. Width: 6.0 mm. Color (both sides): RHS 137C. Margin: Entire. Apex: Acuminate. Texture (both sides): Strigose.

Receptacle:

*Width*.—9.0 mm.

*Depth*.—7.0 mm.

*Color*.—RHS NN155A.

Seeds:

*Length*.—2.0 mm.

*Width*.—0.75 mm.

*Color*.—RHS 203B.

Pests/diseases: No unusual resistance or susceptibility noted to date.

I claim:

1. A new and distinct variety of *Rudbeckia* plant named 'Sun Stream', substantially as illustrated and described herein.

* * * * *